US009375352B2

(12) United States Patent
Robinson et al.

(10) Patent No.: US 9,375,352 B2
(45) Date of Patent: Jun. 28, 2016

(54) REDUCED-PRESSURE WOUND TREATMENT SYSTEMS AND METHODS EMPLOYING MANIFOLD STRUCTURES

(71) Applicant: KCI Licensing, Inc., San Antonio, TX (US)

(72) Inventors: Timothy Mark Robinson, Basingstoke (GB); Christopher Brian Locke, Bournemouth (GB); Aidan Marcus Tout, Alderbury (GB)

(73) Assignee: KCI Licensing, Inc., San Antonio, TX (US)

( * ) Notice: Subject to any disclaimer, the term of this patent is extended or adjusted under 35 U.S.C. 154(b) by 223 days.

(21) Appl. No.: 14/205,688

(22) Filed: Mar. 12, 2014

(65) Prior Publication Data
US 2014/0194837 A1   Jul. 10, 2014

Related U.S. Application Data

(62) Division of application No. 12/639,288, filed on Dec. 16, 2009, now Pat. No. 8,708,984.

(60) Provisional application No. 61/140,664, filed on Dec. 24, 2008.

(51) Int. Cl.
*A61F 13/00* (2006.01)
*A61F 13/02* (2006.01)
*A61M 1/00* (2006.01)

(52) U.S. Cl.
CPC ....... *A61F 13/00068* (2013.01); *A61F 13/0203* (2013.01); *A61F 13/0216* (2013.01); *A61M 1/0023* (2013.01); *A61M 1/0088* (2013.01)

(58) Field of Classification Search
CPC ........... A61F 13/00068; A61F 13/0203; A61F 13/0216; A61M 1/2023; A61M 1/0088
See application file for complete search history.

(56) References Cited

U.S. PATENT DOCUMENTS 1,355,846 A   10/1920  Rannells
2,547,758 A   4/1951   Keeling
(Continued)

FOREIGN PATENT DOCUMENTS

AU   550575 A1   3/1986
AU   745271      4/1999
(Continued)

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (and certified translation).
(Continued)

*Primary Examiner* — Leslie Deak
*Assistant Examiner* — Kai Weng

(57) ABSTRACT

Manifold structures, systems, and methods are disclosed that include using longitudinal members and one or more shaped projections to cause microstrain at a tissue site. In one instance a manifold structure includes a plurality of spaced longitudinal members and at least one shaped projection coupled to at least one of the plurality of longitudinal members for creating a microstrain at a tissue site. The at least one shaped projection includes a columnar member having a distal end and includes an enlarged member positioned at the distal end of the columnar member. The columnar member has a first outer diameter ($D_1$) and the enlarged member has a second outer diameter ($D_2$). The second outer diameter of the enlarged member is greater than the first outer diameter of the columnar member ($D_2 > D_1$). Other systems, methods, and structures are presented.

8 Claims, 9 Drawing Sheets

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,398,910 A * | 8/1983 | Blake ............ A61M 25/0071 604/266 |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2006/0079852 A1 | 4/2006 | Bubb et al. |
| 2008/0275409 A1 * | 11/2008 | Kane ............ A61F 13/0203 604/305 |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 4/2002 |
| WO | 80/02182 | 10/1980 |
| WO | 87/04626 | 8/1987 |
| WO | 90/10424 | 9/1990 |
| WO | 93/09727 | 5/1993 |
| WO | 94/20041 | 9/1994 |
| WO | 96/05873 | 2/1996 |
| WO | 97/18007 | 5/1997 |
| WO | 99/13793 | 3/1999 |

OTHER PUBLICATIONS

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.

(56) References Cited

OTHER PUBLICATIONS

S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Đ ukić, Ž. Maksimović, Đ . Radak, and P. Peška, "Vacuum Therapy in the Treatment of Peripheral Blood Vessels," Timok Medical Journal 11 (1986), pp. 161-164 (and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007).

* cited by examiner

REDUCED-PRESSURE WOUND TREATMENT SYSTEMS AND METHODS EMPLOYING MANIFOLD STRUCTURES

RELATED APPLICATIONS

This application is a division of U.S. patent application Ser. No. 12/639,288, entitled "Reduced-Pressure Wound Treatment Systems and Methods Employing Manifold Structures," filed Dec. 16, 2009, which claims the benefit, under 35 U.S.C. §119(e), of the filing of U.S. Provisional Patent Application Ser. No. 61/140,664, entitled "Reduced-Pressure Wound Treatment Systems and Methods Employing A Microstrain-Inducing Manifold," filed Dec. 24, 2008. Each of the above applications are incorporated herein by reference for all purposes.

BACKGROUND

The present invention relates generally to medical treatment systems and, more particularly, to reduced-pressure wound treatment systems and methods employing manifold structures.

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "NPWT," "reduced pressure therapy," or "vacuum therapy") provides a number of benefits, which may include faster healing and increased formulation of granulation tissue.

Negative pressure therapy, or reduced-pressure therapy, has been used to promote healing across a wide range of wound types. Typically, an open-cell foam is placed directly into the wound bed. A drape is then used to cover the dressing and seal the wound. The sealing member is then fluidly coupled to a reduced-pressure therapy unit to provide negative pressure, or reduced pressure, to the wound through the foam. While this approach has produced meaningful results, shortcomings and areas of desired of improvement remain.

BRIEF SUMMARY

Shortcomings with wound care systems and methods are addressed by the illustrative embodiments herein. According to an illustrative, non-limiting embodiment, a reduced-pressure wound treatment system for treating a tissue site on a patient includes a manifold structure for disposing proximate the tissue site. The manifold structure includes a plurality of spaced longitudinal members and at least one shaped projection coupled to at least one of the plurality of longitudinal members for creating a microstrain at the tissue site. The at least one shaped projection includes a columnar member having a distal end and includes an enlarged member positioned at the distal end of the columnar member. The columnar member has a first outer diameter ($D_1$) and the enlarged member has a second outer diameter ($D_2$). The second outer diameter of the enlarged member is greater than the first outer diameter of the columnar member ($D_2 > D_1$). The system further includes a sealing member for placing over the tissue and manifold structure and a reduced-pressure subsystem for delivering reduced pressure to the sealing member.

According to another illustrative, non-limiting embodiment, a manifold structure for treating a tissue site on a patient includes a plurality of spaced longitudinal members and at least one shaped projection coupled to at least one of the plurality of longitudinal members for creating a microstrain at the tissue site. The at least one shaped projection includes a columnar member having a distal end and includes an enlarged member positioned at the distal end of the columnar member. The columnar member has a first outer diameter ($D_1$) and the enlarged member has a second outer diameter ($D_2$). The second outer diameter of the enlarged member is greater than the first outer diameter of the columnar member ($D_2 > D_1$).

According to another illustrative, non-limiting embodiment, a method for treating a tissue site on a patient with reduced pressure includes placing a manifold structure proximate the tissue of a patient, disposing a sealing member over the manifold structure and the patient's skin; and forming a fluid seal between the sealing member and the patient's skin. The method further includes providing reduced pressure to the manifold structure whereby the at least one shaped projection creates microstrain at the tissue site. The manifold structure includes a plurality of spaced longitudinal members and at least one shaped projection coupled to at least one of the plurality of longitudinal members for creating a microstrain at the tissue site. The at least one shaped projection includes a columnar member having a distal end and includes an enlarged member positioned at the distal end of the columnar member. The columnar member has a first outer diameter ($D_1$) and the enlarged member has a second outer diameter ($D_2$). The second outer diameter of the enlarged member is greater than the first outer diameter of the columnar member ($D_2 > D_1$).

Other features and advantages of the illustrative embodiments will become apparent with reference to the drawings and detailed description that follow.

BRIEF DESCRIPTION OF THE DRAWINGS

A more complete understanding of the present invention may be obtained by reference to the following Detailed Description when taken in conjunction with the accompanying Drawings wherein.

DETAILED DESCRIPTION

Figure 1:
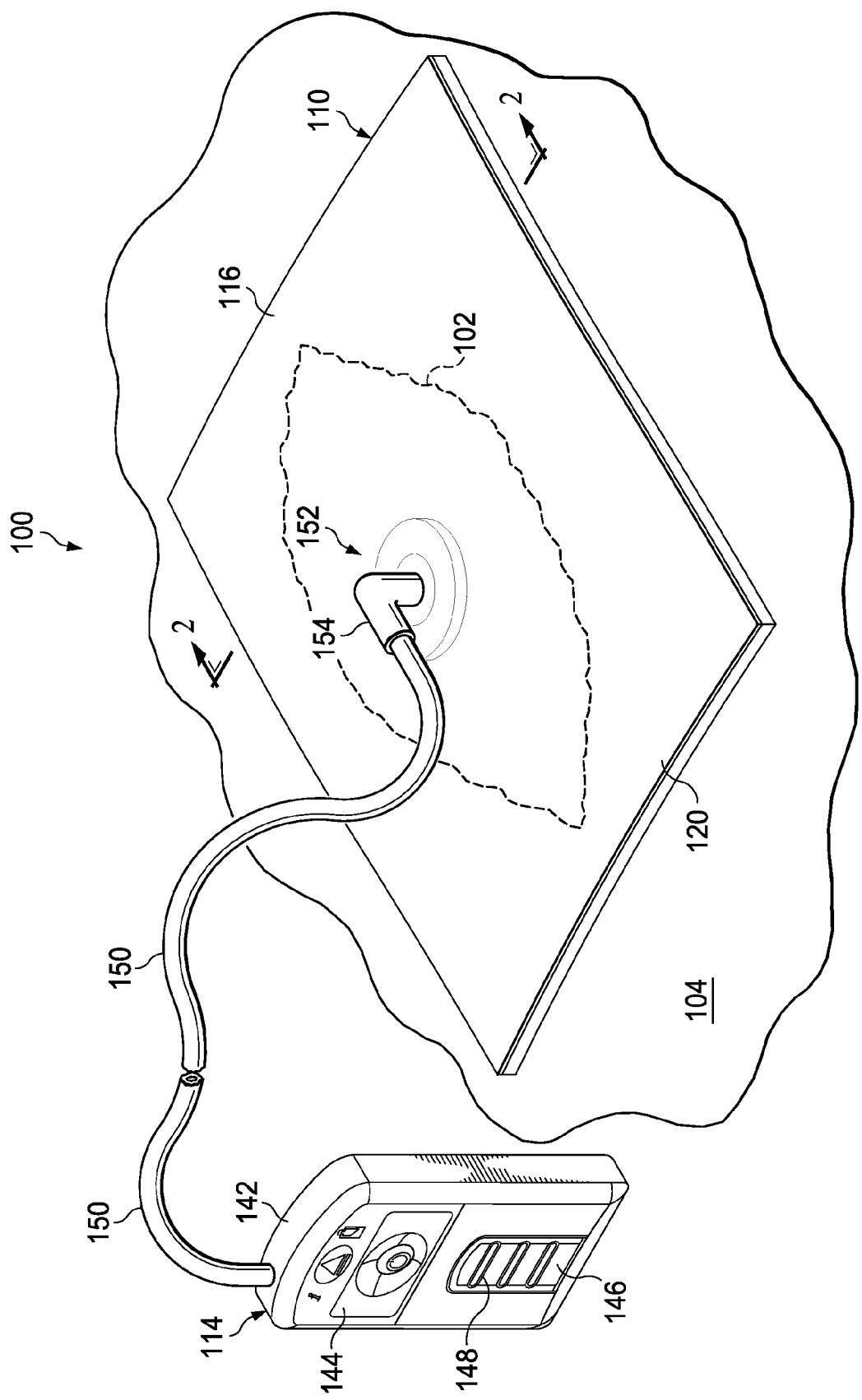
FIG. 1 is a schematic, perspective view of an illustrative, non-limiting embodiment of a reduced-pressure wound treatment system for treating a wound on a patient shown over a wound.

In the following detailed description of the preferred embodiments, reference is made to the accompanying drawings that form a part hereof, and in which is shown, by way of illustration, specific embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the invention, the description may omit certain information known to those skilled in the art. The following detailed description is, therefore, not to be taken in a limiting sense, and the scope of the present invention is defined only by the appended claims.

Referring now primarily to FIGS. 1-3B, an illustrative, non-limiting embodiment of a reduced-pressure wound treatment system 100 for treating a tissue site 103 on a patient is presented. The tissue site 103 may be, for example, a wound 102, or damaged area of tissue, on a patient. The tissue site 103 may be the bodily tissue of any human, animal, or other organism, including bone tissue, adipose tissue, muscle tissue, dermal tissue, vascular tissue, connective tissue, cartilage, tendons, ligaments, or any other tissue. Unless otherwise indicated, as used herein, "or" does not require mutual exclusivity. While the reduced-pressure wound treatment system 100 is shown in the context of the wound 102, it will be appreciated that the reduced-pressure wound treatment system 100 may be used to treat many different types of tissue sites 103 and wounds including area wounds, incisions, internal wounds, or other tissue sites. The reduced-pressure wound treatment system 100 is shown on the wound 102, which is through the epidermis 104, or generally skin, and the dermis 106 and reaching into a hypodermis, or subcutaneous tissue 108.

The reduced-pressure wound treatment system 100 generally includes a sealing member 110, a microstrain-inducing manifold 112, and a reduced-pressure subsystem 114. As will be described further below, in operation the microstrain-inducing manifold 112 induces microstrain and may be referred to, as a microstrain-inducing manifold. The microstrain-inducing manifold 112 has a first side 113 and a second, patient-facing side 115.

Among the numerous benefits of the reduced-pressure wound treatment system 100 is the biological response initiated by microstrain within the wound 102. Microstrain results from pressure distributed with the microstrain-inducing manifold 112 to a tissue site 103, such as a wound surface 105 of the wound 102. It is believed that this action creates areas of cell surface strain, or microdeformation. The cells appear to respond to the strain by expressing special receptors on the surface of the cells and turning on genetic pathways in the cells, which promote healing activities. The healing activities may include increased metabolic activity, stimulation of fibroblast migration, increased cellular proliferation, extra cellular matrix production, and the formation of granulation tissue, as well as a decrease in edema and a subsequent improvement of perfusion at the tissue site 103. With respect to the wound 102, over time, granulation tissue fills the wound 102 and thereby further reduces volume and prepares the wound 102 for final closure by secondary or delayed primary intention.

The sealing member 110 is generally formed from a flexible sheet. The sealing member 110 includes a first surface 120 and a patient-facing surface 122. The sealing member 110 may be sized so that the sealing member 110 overlaps the wound 102 in such a manner that a drape extension 116 extends beyond the peripheral edge of the wound 102.

The sealing member 110 may be formed from any material that provides a fluid seal. As used herein, "fluid seal," or "seal," means a seal adequate to maintain reduced pressure at a desired site, e.g., a tissue site, given the particular reduced-pressure source involved. The sealing member may, for example, be an impermeable or semi-permeable, elastomeric material. "Elastomeric" means having the properties of an elastomer. Elastomeric generally refers to a polymeric material that has rubber-like properties. More specifically, most elastomers have ultimate elongations greater than 100% and a significant amount of resilience. The resilience of a material refers to the material's ability to recover from an elastic deformation. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane, EVA film, co-polyester, and silicones. Specific examples of sealing member materials include a silicone drape, 3M Tegaderm® drape, acrylic drape such as one available from Avery Dennison, or an incise drape.

An attachment member 118 or device may be coupled to the sealing member 110. The attachment member 118 is operable to removably couple the sealing member 110 to a patient's epidermis 104. As used herein, the term "coupled" includes coupling via a separate object and includes direct coupling. The term "coupled" also encompasses two or more components that are continuous with one another by virtue of each of the components being formed from the same piece of material. Also, the term "coupled" may include chemical, such as via a chemical bond, mechanical, thermal, or electrical coupling. Fluid coupling means that fluid is in communication between the designated parts or locations. The sealing member 110 and attachment member 118 work together to form a fluid seal over the patient's epidermis 104. The attachment member 118 may be any material suitable to help couple the sealing member 110 to a patient's epidermis 104. For example, the attachment member 118 may be a pressure-sensitive adhesive, heat-activated adhesive, sealing tape, double-sided sealing tape, paste, hydrocolloid, hydrogel, hooks, sutures, etc.

In the illustrative embodiment, the attachment member 118 is an adhesive layer 119 coupled to the patient-facing surface 122 of the drape extension 116. The attachment member 118 may span the entire width or a portion of the patient-facing surface 122 of the sealing member 110. Alternatively, in the case of sealing tape, the attachment member 118 may be applied over the entire first surface 120 of the sealing member 110, or over the first surface of the drape extensions 116.

The microstrain-inducing manifold 112 is typically positioned between the second, patient-facing surface 122 of the sealing member 110 and the tissue site 103, e.g., the wound 102. The microstrain-inducing manifold 112 may be sized to approximate the estimated area of the wound 102, although a larger or smaller size may be used in different applications. In the illustrative embodiment, the microstrain-inducing manifold 112 includes a plurality of interconnected nodes 124. The interconnected nodes 124 may have a substantially circular cross-section, but it will be appreciated that the interconnected nodes 124 may have any suitable cross-section including, but not limited to, triangular, square, rectangular, hexagonal, octagonal, elliptical, etc.

Each interconnected node 124 may include one or more shaped projections 126. The shaped projections 126 are operable to create microstrain at the cellular level within the tissue site 103, e.g., the wound 102. While the illustrative embodiment shows each interconnected node 124 having a plurality of shaped projections 126, it will be appreciated that some interconnected nodes 124 may be formed to avoid creating microstrains in certain areas. For example, one or more shaped projections 126 may be formed with a lower profile in a certain area or be absent all together in certain areas. Moreover, an additional manifold with no shaped projections, e.g., a smooth, laminar manifold, may be placed between at least a portion of the shaped projections 126 of the microstrain-inducing manifold 112 and a portion of the tissue site 103 to prevent the creation of strain in a certain area. It is believed that avoiding microstrains in certain areas is helpful to overall patient care. For example, it may be desirable to have a microstrain-inducing manifold 112 without projections 126 or that does not create microstrains in certain areas if a portion of the microstrain-inducing manifold 112 will lay on top of a vein, an artery, graft(s), objects used for adjunctive treatment or therapy (e.g., stents), exposed organs (e.g., heart or bowel), etc.

The shaped projections 126 may be substantially the same size. Alternatively, some projections 126 may be larger or smaller than others. In one alternative, some shaped projections 126 may have a larger pitch than others, where "pitch" is defined by the angle 128 between a reference line 127 formed to have a right angle with a longitudinal axis 129 of the shaped projection 126 as shown in cross section in FIG. 3C. Each shaped projection 126 has an outer surface 130 and a base 132. While the shaped projections 126 in the illustrative embodiment are conical in shape, it will be appreciated that the shaped projections 126 may have any suitable shape capable of creating a microstrain within the wound 102; for example, the shaped projections 126 may be substantially cube shaped, pyramid shaped, hemispherically shaped, cylindrically shaped, triangularly shaped, cylindrically shaped with a distal recess, tapered, more elaborately shaped, etc. The shaped projections 126 are typically tapered from a thick proximal end to a thin distal end or vice versa. In one embodiment, the shaped projections 126 are formed of the same material as the interconnected nodes 124. Alternatively, at least some of the shaped projections 126 may be formed from a different material or the same material type of material with different properties than the interconnected nodes 124 or the other shaped projections 126. Via material selection, one may control the stiffness of the interconnected nodes 124 such that greater microstrain may be provided in certain areas of the wound 102 versus others. The interconnected nodes 124, shaped projections 126, and the microstrain-inducing manifold 112 generally may be formed of a foam material or a non-foam material.

The interconnected nodes 124 may be interconnected using a network of connecting members 134. For example, the network of connecting members 134 may include a plurality of members 136 with each member 136 coupling adjacent interconnected nodes 124 to one another. In the illustrative embodiment, the members 136 have a substantially circular cross-section; however, it will be appreciated that the members 136 may have any suitable cross-section, including, but not limited to, triangular, square, rectangular, hexagonal, octagonal, elliptical, etc. In addition, as will be discussed below, the connecting members 134 may be configured such that the microstrain-inducing manifold 112 behaves anisotropically when subjected to a reduced pressure.

The interconnected nodes 124, connecting members 134, and shaped projections 126 are arranged such that the microstrain-inducing manifold 112 includes a plurality of flow channels 140 (FIG. 3B) or pathways between the interconnected nodes 124. The flow channels 140 improve distribution of fluids provided to and removed from the area of tissue around the microstrain-inducing manifold 112. Thus, the microstrain-inducing manifold 112 is operable to assist in applying reduced pressure to, delivering fluids to, or removing fluids from a tissue site 103. Moreover, the design of microstrain-inducing manifold 112 helps to avoid painful removal caused by in-growth, i.e., when growth of granulation tissue occurs into a manifold, and allows for easier removal from the tissue site 103.

The microstrain-inducing manifold 112 may be formed from any suitable material. By way of example only, and without limitation, the microstrain-inducing manifold 112 may be formed from an elastomer, a bioabsorbable/biodegradable polymer, etc. In addition, the manifold material may itself be, or may be combined with, a radio opaque material or a UV florescent material such that the wound 102 may be scanned with an X-ray or UV light in order to determine whether or not any remnants of the microstrain-inducing manifold 112 remain in the wound 102 after efforts have been made to remove the microstrain-inducing manifold 112 from the wound 102. Additionally, the shaped projections 126, or microstrain-inducing manifold 112 as a whole, may be coated with a drug (e.g., an anticoagulant), an antimicrobial agent (e.g., silver or copper), a hydrophilic material, etc. Optionally, the microstrain-inducing manifold 112 may also be formed with additional components, e.g., a delivery tube (not shown), whereby drugs or antimicrobial agents may be delivered to the wound 102 through the microstrain-inducing manifold 112.

The microstrain-inducing manifold 112 may be formed by any suitable process, including, but not limited to, micromolding, injection molding, casting, etc. The shaped projections 126 may be formed to be substantially integral with corresponding interconnected nodes 124 or may be coupled to corresponding interconnected nodes 124 by any suitable technique, including, but not limited to, mechanical fasteners, welding (e.g., ultrasonic or RF welding), bonding, adhesives, cements, etc.

The microstrain-inducing manifold 112 may include numerous devices for creating point pressure or otherwise inducing microstrain. In one illustrative, non-limiting embodiment, the microstrain-inducing manifold 112 includes limited contact points with the tissue site 103. The contact points contribute to the inducement of microstrain at the tissue site 103. Thus, in one illustrative, non-limiting embodiment, the microstrain-inducing manifold 112 adjacent the tissue site 103 may have a projection surface area of X cm$^2$ associated with the second, patient-facing side, and yet the portion of the microstrain-inducing manifold 112 directly impinging on the tissue site 103 may be less than 40 percent of the surface area X (40% X). As used herein, "projection surface area" means the area that a general projection of an item would make on a flat surface.

In another illustrative, non-limiting embodiment, the microstrain-inducing manifold 112 adjacent the tissue site 103 may have a projection surface area of X cm² associated with the second, patient-facing side, and yet the portion of the microstrain-inducing manifold 112 directly impinging on the tissue site 103 may be less than 30 percent of the surface area X (30% X). In another illustrative, non-limiting embodiment, the microstrain-inducing manifold 112 adjacent the tissue site 103 may have a projection surface area of X cm² associated with the second, patient-facing side, and yet the portion of the microstrain-inducing manifold 112 directly impinging on the tissue site 103 may be less than 20 percent of the surface area X (20% X). In one illustrative, non-limiting embodiment, the microstrain-inducing manifold 112 adjacent the tissue site 103 may have a projection surface area of X cm² associated with the second, patient-facing side, and yet the portion of the microstrain-inducing manifold 112 directly impinging on the tissue site 103 may be less than 10 percent of the surface area X (10% X). In one illustrative, non-limiting embodiment, the microstrain-inducing manifold 112 adjacent the tissue site 103 may have a projection surface area of X cm² associated with the second, patient-facing side, and yet the portion of the microstrain-inducing manifold 112 directly impinging on the tissue site 103 may be less than 5 percent of the surface area X (5% X).

In still another illustrative, non-limiting embodiment, the microstrain-inducing manifold 112 adjacent the tissue site 103 may have a projection surface area of X cm² associated with the second, patient-facing side, and yet the portion of the microstrain-inducing manifold 112 directly impinging on the tissue site 103 may be less than 2 percent of the surface area X (2% X). In one illustrative, non-limiting embodiment, the microstrain-inducing manifold 112 adjacent the tissue site 103 may have a projection surface area of X cm² associated with the second, patient-facing side, and yet the portion of the microstrain-inducing manifold 112 directly impinging on the tissue site 103 may be less than 1 percent of the surface area X (1% X). In one illustrative, non-limiting embodiment, the microstrain-inducing manifold 112 adjacent the tissue site 103 may have a projection surface area of X cm² associated with the second, patient-facing side, and yet the portion of the microstrain-inducing manifold 112 directly impinging on the tissue site 103 may be less than 0.5 percent of the surface area X (0.5% X).

Figure 2:
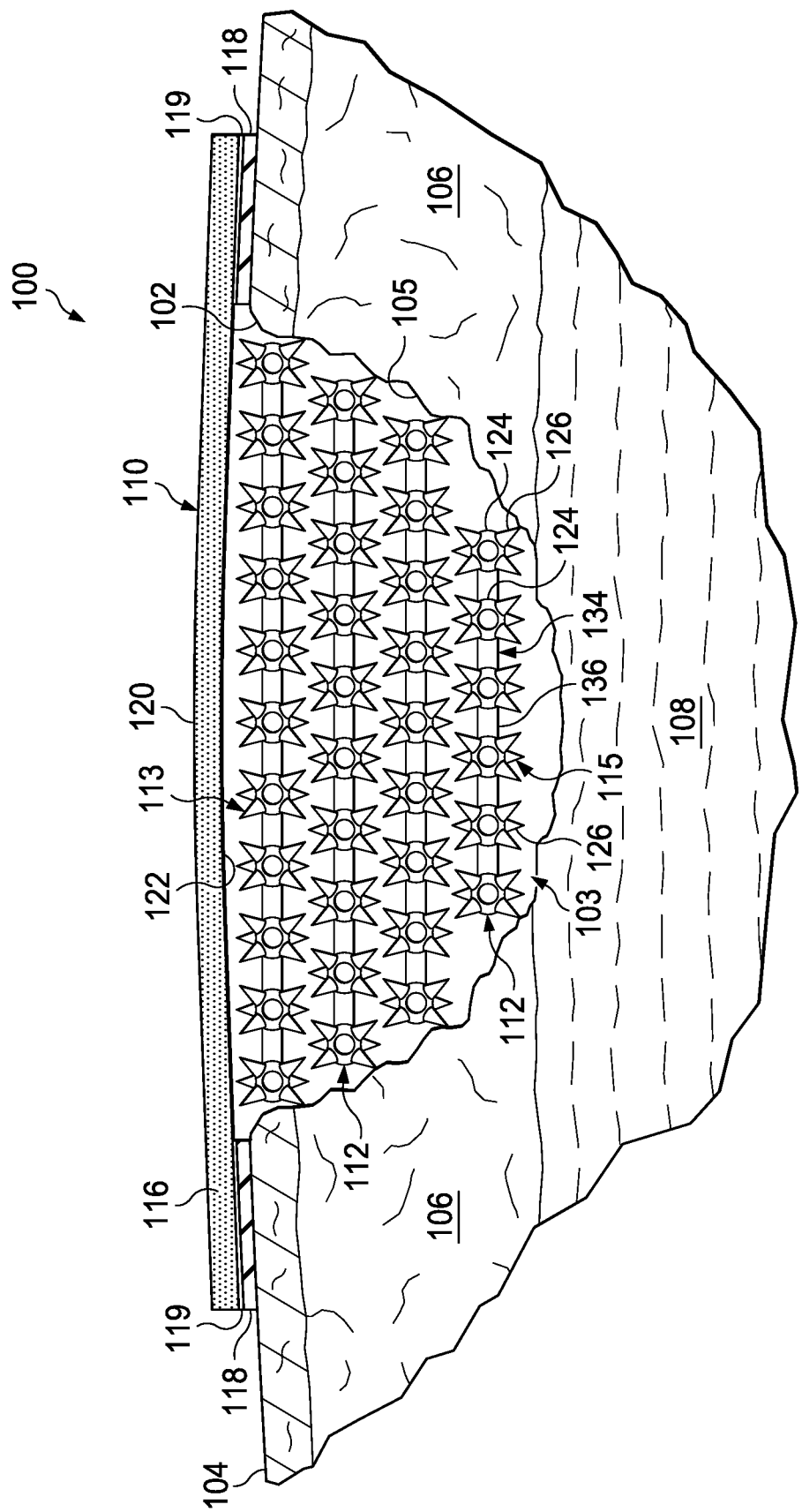
FIG. 2 is a schematic, cross-sectional view of a portion of the system of FIG. 1 taken along line 2-2 in FIG. 1.
Figure 3A:
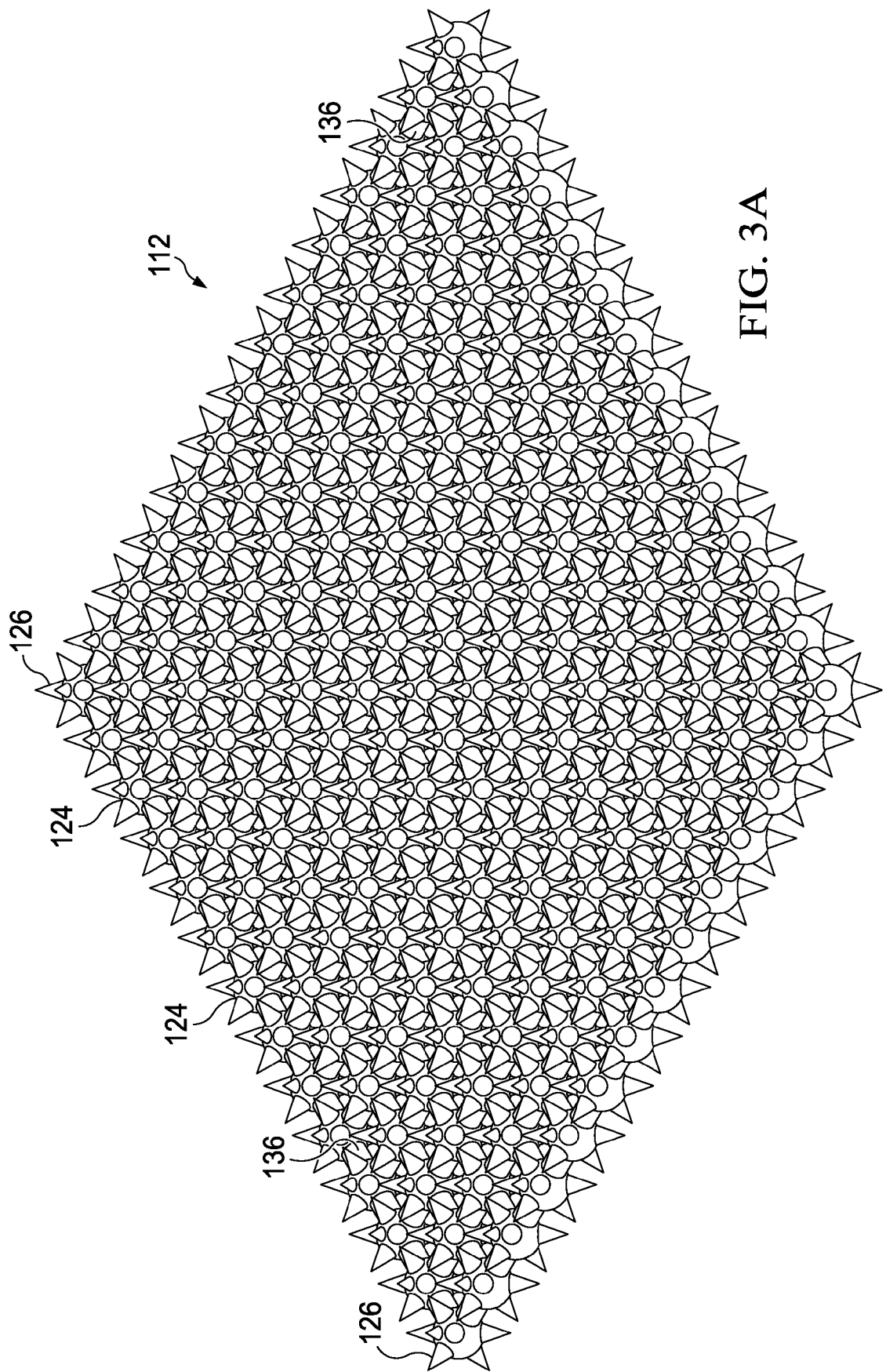
FIG. 3A is a schematic, perspective view of an illustrative, non-limiting embodiment of a microstrain-inducing manifold for use in treating a tissue site, such as a wound, on a patient as part of an illustrative, non-limiting embodiment of a reduced-pressure wound treatment system.
Figure 3B:
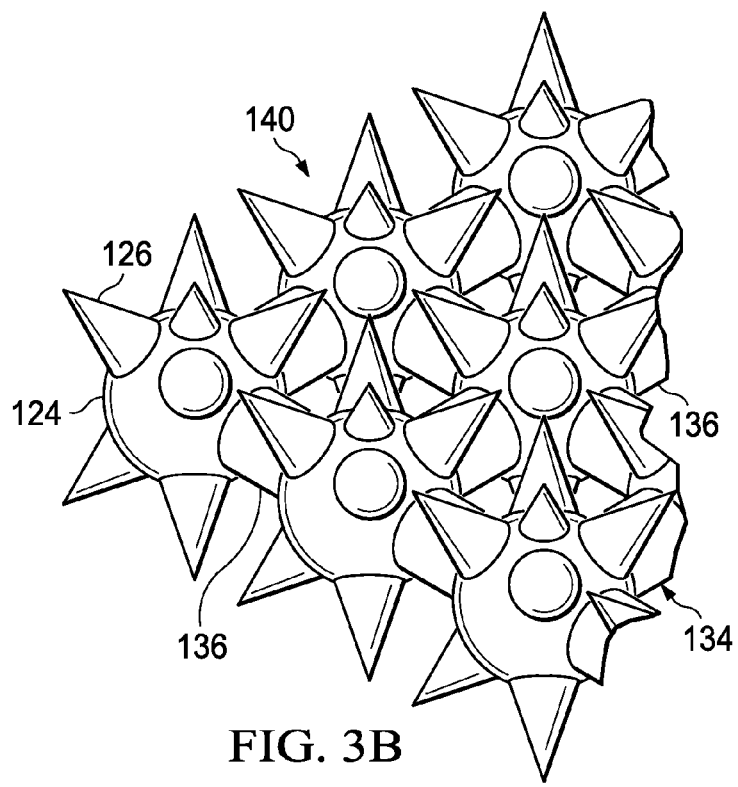
FIG. 3B is an enlarged detail of the perspective view of FIG. 3A.
Figure 3C:
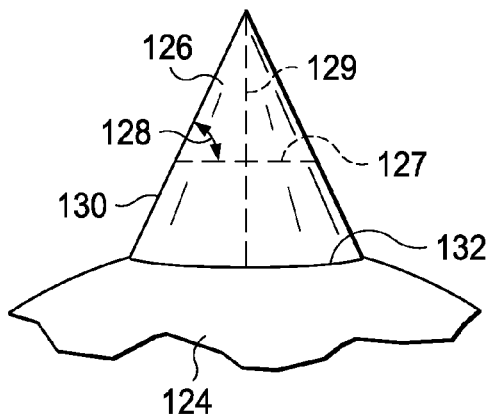
FIG. 3C is a side view of a portion of an interconnected node and shaped projection of the microstrain-inducing manifold shown in FIGS. 3A and 3B.

In one illustrative, non-limiting embodiment, the microstrain-inducing manifold 112 adjacent the tissue site 103 may have a projection surface area of X cm² associated with the second, patient-facing side, and yet the portion of the microstrain-inducing manifold 112 directly impinging on the tissue site 103 may be less than 0.2 percent of the surface area X (0.2% X). Referring to FIG. 2, the microstrain-inducing manifold 112 adjacent to tissue site 103 103, e.g., wound surface 105, may cover the wound surface 105, and may have a projection surface area X, and yet the portion of microstrain-inducing manifold 112 directly impinging on the wound surface 105 may only be 0.2 percent of X. Referring to FIG. 3C, it should be understood that the impinging portion may only be a portion of an outer surface 130 of each of the plurality of shaped projections 126.

The microstrain-inducing manifold 112 may be disposed proximate the wound 102 such that the interconnected nodes 124 engage the wound surface 105. In one illustrative embodiment, the microstrain-inducing manifolds 112 are stacked on top of one another to substantially fill the wound 102. However, it will be appreciated that a single microstrain-inducing manifold 112 may be employed or a multi-layer microstrain-inducing manifold may also be formed and used. The microstrain-inducing manifold 112 may be formed from a single interconnected node 124 with a shaped projection 126; multiple independent interconnected nodes 124 with shaped projections 126; or a group of interconnected nodes 124, which include shaped projections 126, that are interconnected with the connecting members 134.

It will also be appreciated that a single microstrain-inducing manifold 112 may be rolled up or folded over itself in order to fill the wound 102. Furthermore, it will be appreciated that a single microstrain-inducing manifold 112 may be loaded into the wound 102 and an additional manifold placed atop the manifold 112. Examples of additional manifolds that may be placed atop the microstrain-inducing manifold 112 include, without limitation, devices that have structural elements arranged to form flow channels, cellular foam such as open-cell foam, porous tissue collections, and liquids, gels and foams that include or cure to include flow channels.

Referring again to FIG. 1, the reduced-pressure subsystem 114 includes a reduced-pressure source 142, which may take many different forms. The reduced-pressure source 142 provides reduced pressure as a part of the reduced-pressure wound treatment system 100. As used herein, "reduced pressure" generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure at the tissue site. Reduced pressure may initially generate fluid flow in the microstrain-inducing manifold 112, a conduit 150, and proximate the tissue site 103. As the hydrostatic pressure around the tissue site 103 approaches the desired reduced pressure, the flow may subside, and the reduced pressure may be maintained. Unless otherwise indicated, values of pressure stated herein are gauge pressures. The reduced pressure delivered may be static or dynamic (patterned or random) and may be delivered continuously or intermittently. Although the terms "vacuum" and "negative pressure" may be used to describe the pressure applied to the tissue site, the actual pressure applied to the tissue site may be more than the pressure normally associated with a complete vacuum. Consistent with the use herein, an increase in reduced pressure or vacuum pressure typically refers to a relative reduction in absolute pressure.

The reduced-pressure subsystem 114 provides reduced pressure. The reduced pressure subsystem 114 includes a reduced-pressure source 142 that may be any source of a reduced pressure, such a vacuum pump, wall suction, etc. While the amount and nature of reduced pressure applied to a tissue site will typically vary according to the application, the reduced pressure will typically be between −5 mm Hg and −500 mm Hg. Pressure may be applied to the microstrain-inducing manifold 112 in other ways as well; for example, a pressure wrap may be used.

In the illustrative embodiment of FIG. 1, the reduced-pressure source 142 is shown having a battery compartment 144 and a canister region 146 with windows 148 providing a visual indication of the level of fluid within canister 146. An interposed membrane filter, such as hydrophobic or oleophobic filter, may be interspersed between the conduit 150, or tubing, and the reduced-pressure source 142.

The reduced pressure supplied by the reduced-pressure source 142 is delivered through the conduit 150 to a reduced-pressure interface 152, which may be an elbow port 154.

In one illustrative embodiment, the port 154 is a TRAC® technology port available from Kinetic Concepts, Inc. of San Antonio, Tex. The reduced-pressure interface 152 allows the reduced pressure to be delivered to the sealing member 110 and realized within an interior portion of sealing member 110 as well as the microstrain-inducing manifold 112. In this illustrative embodiment, the port 154 extends through the sealing member 110 to the microstrain-inducing manifold 112.

In use, the reduced-pressure wound treatment system 100 may be applied to a patient's epidermis 104 over the tissue site 103, e.g., wound 102. The microstrain-inducing manifold 112 may be disposed proximate the tissue site 103, e.g., disposed within the wound 102, or may overlay a portion of the wound 102. The sealing member 110 may be placed over the top of the microstrain-inducing manifold 112 such that drape extensions 116 extend beyond the periphery of the wound 102. The drape extensions 116 are secured to the patient's epidermis 104 (or a gasket member, such an additional piece of over drape surrounding the wound edges) by the attachment member 118 in order to form a fluid seal over the wound 102. As used herein, reference to forming a fluid seal with the patient's epidermis shall be deemed to also include forming a seal with a gasket proximate the wound 102.

The reduced-pressure interface 152 is applied, if not already installed, and the conduit 150 fluidly coupled at one end to the reduced-pressure interface 152. The other end of the conduit 150 is fluidly coupled to the reduced-pressure source 142. The reduced-pressure source 142 may be activated such that reduced pressure is delivered to the sealing member 110 and microstrain-inducing manifold 112. The reduced pressure provides reduced-pressure treatment to the tissue site 103, removes fluids, and may force the shaped projections 126 of the microstrain-inducing manifold 112 against the wound 102 such that they create a microstrain at the cellular level within the wound 102. As previously suggested, the microstrain may promote cellular proliferation, formation of granular tissue, and other beneficial effects. Alternatively, the microstrain-inducing manifold 112 may be placed proximate the tissue site 103 and then pressure may be applied by using a wrap over the microstrain-inducing manifold 112 or other source of pressure.

Figure 4A:
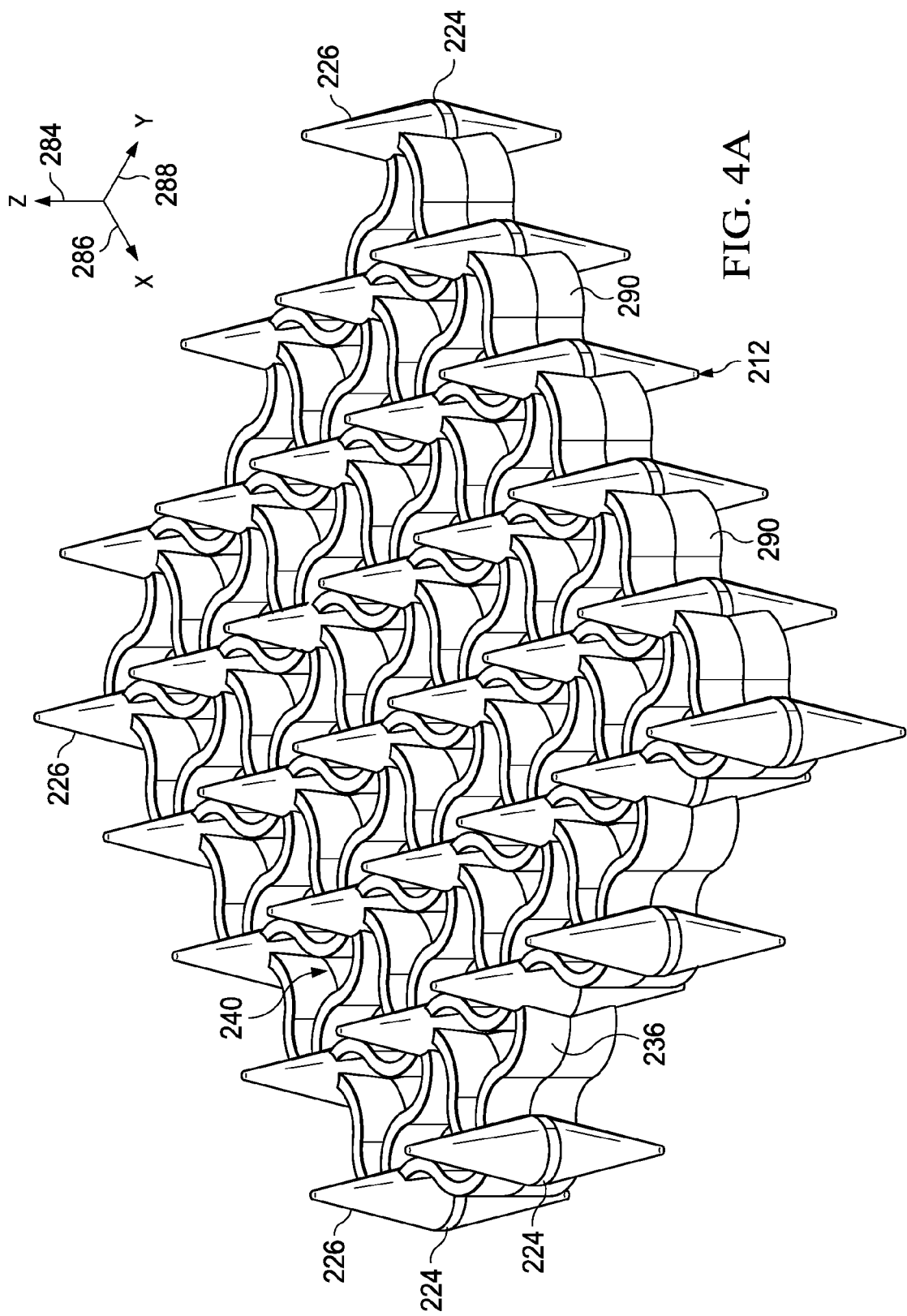
FIG. 4A is a schematic, perspective view of an illustrative, non-limiting embodiment of a microstrain-inducing manifold for use in treating a tissue site.
Figure 4B:
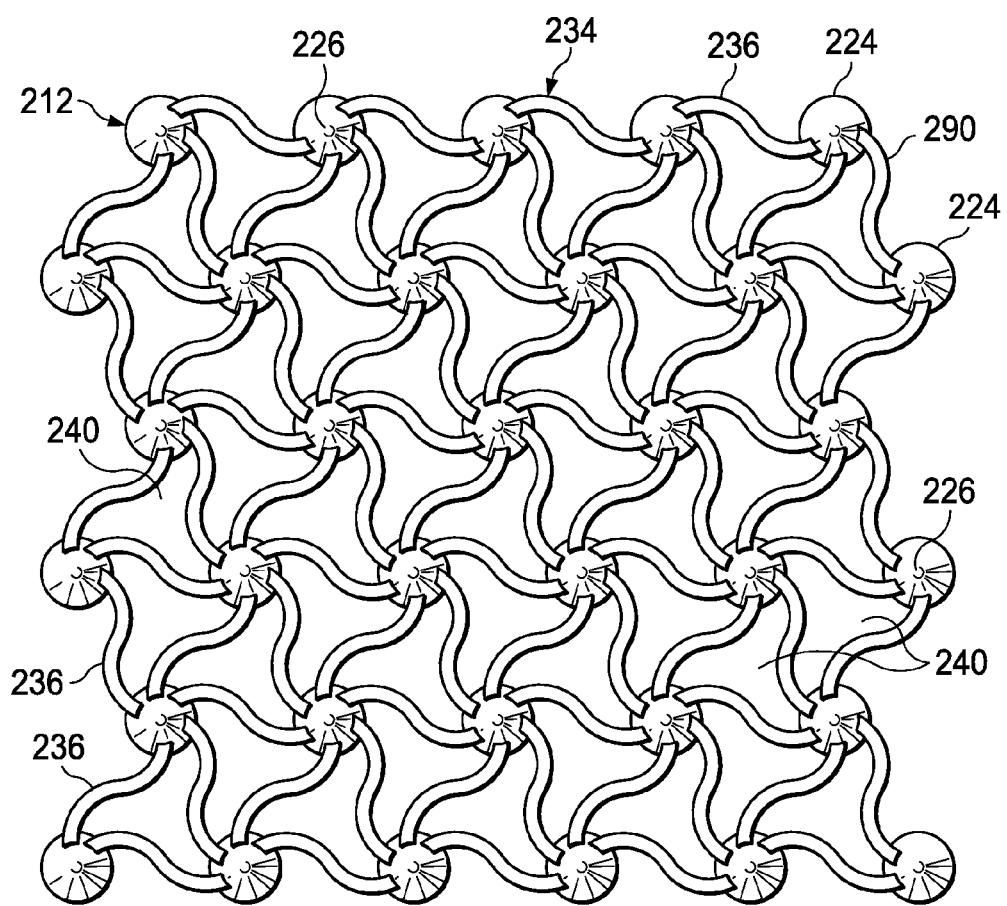
FIG. 4B is a schematic, top view of the microstrain-inducing manifold of FIG. 4A.

Referring now primarily to FIGS. 4A and 4B, an illustrative, non-limiting embodiment of a microstrain-inducing manifold 212 for use as part of a reduced-pressure wound treatment, such as the reduced-pressure wound treatment system 100 in FIG. 1, is shown. The microstrain-inducing manifold 212 includes interconnected nodes 224, which include shaped projections 226 extending from the interconnected nodes 224. In the illustrative embodiment, the shaped projections 226 are conical in shape; however, it will be appreciated that the shaped projections 226 may be any suitable shape capable of creating microstrain within a wound as previously discussed. Moreover, while each interconnected node 224 of the illustrative embodiment includes two projections 226 (one directed up and one directed down for the orientation shown in FIG. 4A), it will be appreciated that any number of projections 224 may extend from each interconnected node 224 or that some of the interconnected nodes 224 may have no projections 224. Also, in the illustrative embodiment, each projection 226 extends substantially normal from a corresponding interconnected node 224, but it will be appreciated that each projection 226 may extend from the corresponding interconnected node 224 at any angle.

The interconnected nodes 224 are spaced apart and interconnected by a network of connecting members 234 as clearly shown in FIG. 4B. The network of connecting members 234 includes a plurality of curved members 236. A plurality of flow channels 240 are formed between the interconnected nodes 224 and members 236. The members 236 have curved surfaces 290 that are curved in a cooperative manner with one another or with the radius of one or more corresponding interconnected nodes 224 such that when the microstrain-inducing manifold 212 is subjected to a reduced pressure, the microstrain-inducing manifold 212 collapses (partially or fully) in two directions (e.g., along the x-axis 286 and y-axis 288) but not at all or to a lesser extent in a third direction (e.g., the z-axis 284). As the microstrain-inducing manifold 212 collapses, each curved surface 290 of each member 236 abuts or approaches a curved surface 290 of an adjacent member 236 or at least one corresponding interconnected node 224. This may be particularly advantageous if the reduced-pressure wound treatment system is configured to assist in drawing the wound together during reduced pressure therapy.

Figure 5A:
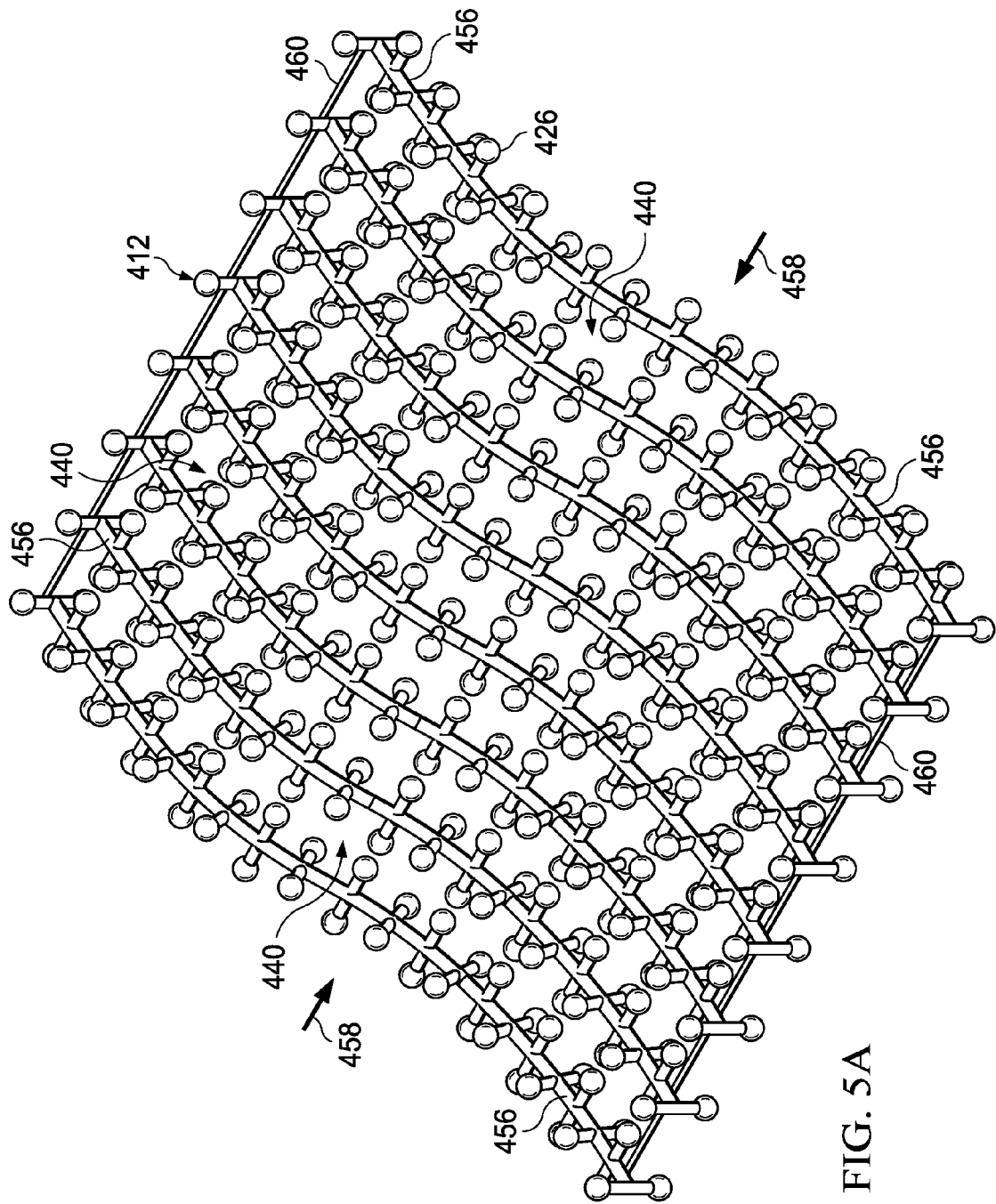
FIG. 5A is a schematic, perspective view of an illustrative, non-limiting embodiment of a microstrain-inducing manifold for use in treating a wound on a patient.
Figure 5B:
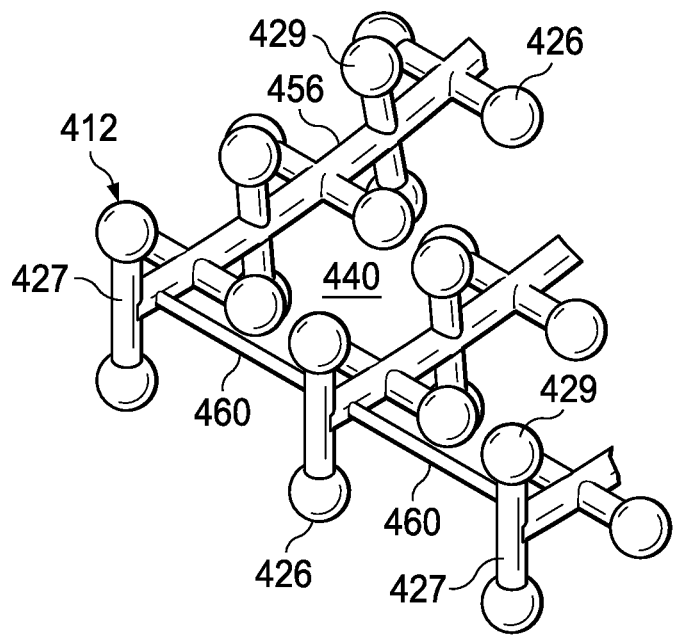
FIG. 5B is an enlarged partial view of the microstrain-inducing manifold of FIG. 5A.

Referring now primarily to FIGS. 5A and 5B, an illustrative, non-limiting embodiment of a manifold structure 412, which is a form of a microstrain-inducing manifold, is presented. The manifold structure 412 is for use with a reduced-pressure wound treatment system, such as the reduced-pressure wound treatment system 100 of FIG. 1, is shown. The manifold structure 412 includes one or more longitudinal members 456. The longitudinal members 456 may be coupled in a spaced relationship by lateral connecting members 460. The lateral connecting members 460 may be coupled to the longitudinal members 456. The longitudinal members 456 and lateral connecting members 460 are shown with circular cross-sections, but it should be appreciated that the longitudinal members 456 and lateral connecting members 460 may have any suitable cross-sectional shape. While reference is made to longitudinal and lateral members, the members 456, 460 need not be orthogonal but may have other relative angles.

Each longitudinal member 456 of the manifold structure 412 includes one or more shaped projections 426 for creating a microstrain within a wound. The longitudinal members 456 and shaped projections 426 are arranged such that the manifold structure 412 includes a plurality of flow channels 440 or pathways between adjacent longitudinal members 456 or between projections 426. The flow channels 440 facilitate distribution of fluids provided to and removed from the area of tissue around the manifold structure 412. It should be understood that any combination of longitudinal members 456 and lateral members 460 may be used. For example, the manifold structure 412 may be formed by a longitudinally connected group of longitudinal members 456 with projections 426. There are eight such longitudinal groups shown in FIG. 5A, and while shown with the lateral connecting members 460, the lateral connecting members 460 may be omitted in some embodiments. Moreover, while only lateral connecting members 460 are shown on the ends, it should be understood that any number of permutations are possible, and lateral members 460 may be distributed at various locations between the longitudinal members 456.

In the illustrative embodiment, each shaped projection 426 projects substantially normal from the corresponding longitudinal member 456. As used here, "normal" is a vector which perpendicular to that surface. For a non-flat surface, the normal vector may be taken at a point and is the same as a normal to the tangent plane at that point. It should be appreciated, however, that each shaped projection 426 may project at any angle relative to the corresponding longitudinal member 456. Each shaped projection 426 may include a columnar body 427, which has a first outer diameter ($D_1$), and an enlarged member 429, which has a second outer diameter ($D_2$). Each enlarged member 429 is positioned at the distal end of an associated columnar body 427. Each columnar body 429 may have any shape, e.g., the cross-section may be a circular, square, elliptical, irregular, etc., and may vary along its longitudinal dimension. The enlarged member 429 may be a spherical member as shown or may take any other shape, such as rounded cylindrical member, a cubical member, or an irregular shape. The second outer diameter ($D_2$) of the enlarged member 429 is greater than the first outer diameter ($D_1$) of the columnar body 427, i.e., $D_2>D_1$. In this regard, the shaped projections 426 may be considered to be tapered from a larger distal end to a smaller proximal end.

Each shaped projection 426 may have any suitable shape capable of creating a microstrain within the wound when the shaped projection 426 impinges upon the wound. Additionally, in the illustrative embodiment, the shaped projections 426 have substantially equal heights, but it will be appreciated that the shaped projections 426 may have varying heights along each longitudinal member 456 or among the plurality of longitudinal members 456. Also, it will be appreciated that certain portions of certain longitudinal members 456 may not have shaped projections 426 such that microstrain is not provided to certain areas within the wound. As with the microstrain-inducing manifolds previously discussed, the manifold structure 412 may be formed using any suitable process, including, but not limited to, micromolding, injection molding, casting, etc. The shaped projections 426 may be formed to be substantially integral with corresponding longitudinal members 456 or may be coupled to corresponding longitudinal members 456 by any suitable technique including, but not limited to, mechanical fasteners, welding (e.g., ultrasonic or RF welding), bonding, adhesives, cements, etc.

In use, the manifold structure 412 is placed proximate the tissue site, e.g., wound, and a sealing member is deployed over the manifold structure 412 and tissue site. Reduced pressure may then be applied or alternatively a direct pressure may be applied. In some embodiments, e.g., embodiment with widely spaced lateral members 460, when the manifold structure 412 is subjected to a reduced pressure, the manifold structure 412 may behave anisotropically. In other words, when the manifold structure 412 is subjected to a reduced pressure, in addition to the shaped projections 426 being forced into the wound to create microstrain, the longitudinal members 456 may move laterally towards each other. Each longitudinal member 456 move closer to an adjacent longitudinal member 456 than the adjacent longitudinal members 456 were prior to the introduction of the reduced pressure. At the same time, the manifold structure 412 does not substantially contract in a direction substantially parallel to the longitudinal members 456.

If the lateral connecting members 460 are omitted, even further contraction may be possible. The manifold structure 412 may deform more in a direction substantially perpendicular to the longitudinal members 456 (as illustrated by arrows 458 in FIG. 5A) without a proportional deformation in the direction parallel with the longitudinal members 456. The deformation is typically within the same plane. This may be advantageous if the system employs other components, such as an anisotropic drape or another manifold, for drawing the wound together during reduced pressure therapy wherein the illustrative manifold structure 412 contracts in a manner complimentary therewith. If spaced lateral connecting members 460 are used in sufficient number, very little contraction may take place. In an alternative embodiment, the manifold structure 412 is configured such that some longitudinal members 456 are arranged substantially perpendicular to other longitudinal members 456 whereby the manifold structure 412 partially contracts, or contracts in a more limited manner, in two directions within the same plane when subjected to a reduced pressure.

Figure 6B:
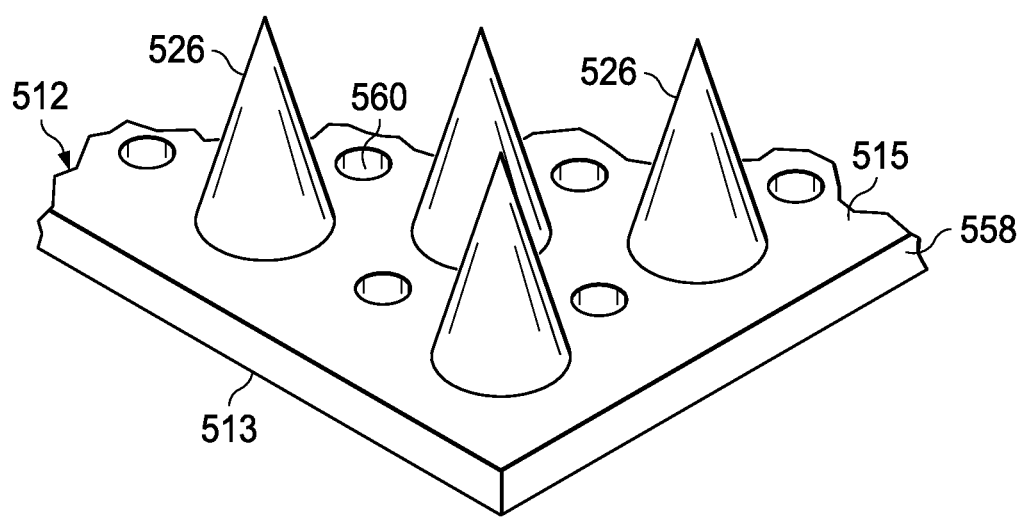
FIG. 6B is an enlarged partial view of the microstrain-inducing manifold of FIG. 6A.
Figure 6A:
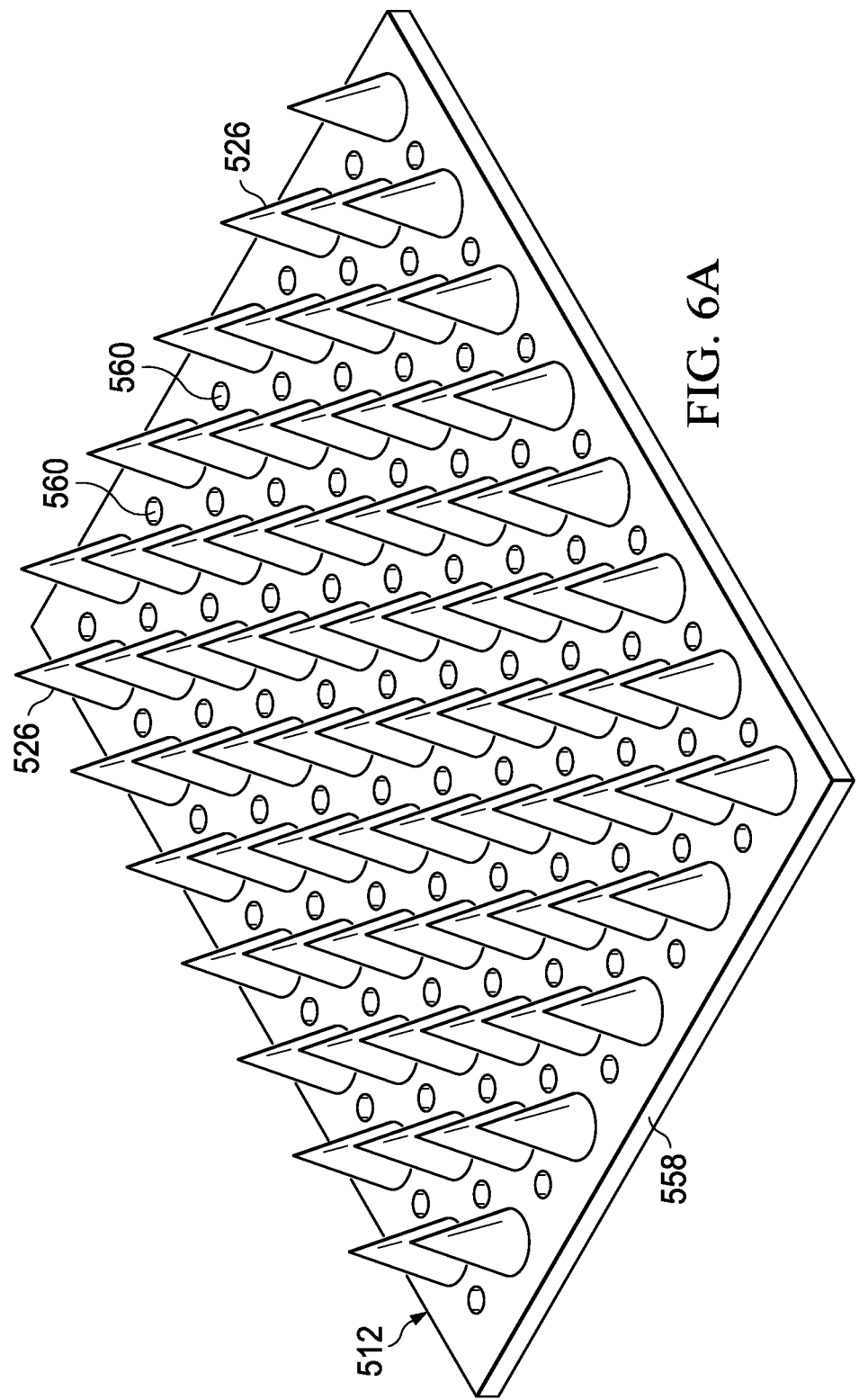
FIG. 6A is a schematic, perspective view of an illustrative, non-limiting embodiment of a microstrain-inducing manifold for use in treating a wound on a patient as part of an illustrative, non-limiting embodiment of a reduced-pressure wound treatment system.

Referring now primarily to FIGS. 6A and 6B, another illustrative, non-limiting embodiment of a microstrain-inducing manifold 512 for use with a reduced-pressure wound treatment system, such as a reduced-pressure wound treatment system 100 (FIG. 1), is shown. The microstrain-inducing manifold 512 includes a mat 558, or base, from which a plurality of shaped projections 526 extend. The mat 558 has a first side 513 and a second, patient-facing side 515. In the illustrative embodiment, the shaped projections 526 are tapered and in particular are substantially conical in shape, but it will be appreciated that the projections 526 may have any suitable shape capable of creating microstrain within the wound. Also, while the illustrative embodiment shows the projections 526 extending substantially normal, i.e., perpendicular, from the mat 558, it will be appreciated that the projections 526 may extend from the mat 558 at any suitable angle. Furthermore, in the illustrative embodiment, the projections 526 have substantially equal heights, but the mat 558 may include projections 526 of varying heights. Portions of the mat 558 may not have any projections such that microstrain is not provided to certain areas within the wound. Additionally, the stiffness of the shaped projections 526 and pitch of the shaped projections 526 may vary along the mat 558 such that the microstrain created by the projections 526 may be greater in certain areas of the wound versus other areas.

The shaped projections 526 may be formed as integral portions of the mat 558 or coupled to the mat 558 by any suitable techniques, including but not limited to mechanical fasteners, welding (e.g., ultrasonic or RF welding), bonding, adhesives, cements, etc. The mat 558 may also includes a plurality of apertures 560 (FIG. 6B) disposed between the projections 526 to improve the distribution of fluids provided to and removed from the area of tissue around the microstrain-inducing manifold 512. In an alternative embodiment, the shaped projections 526 may be formed from a modified honey on the mat 558. The honey may be modified so that it is solid or partially solid and retains its shape for at least a certain amount of time whilst engaging the wound. Advantageously, the honey may act as an antimicrobial agent and may be absorbed by the patient after a period of time. Other dissolvable substances may be used as well.

In operation, the microstrain-inducing manifold 512 is typically placed proximate the tissue site with the second, patient-facing side 515 facing the patient and covered with a sealing member. Reduced pressure is then delivered to the microstrain-inducing manifold 512. When subjected to a reduced pressure, the microstrain-inducing manifold 512 impinges on the wound whereby the shaped projections 526 create microstrain within the wound. Additionally, exudate and other fluids pass through the mat 558 via the apertures 560. Also, in some instances, it may be desirable to avoid increasing microstrain within the wound via the shaped projections 526. In such an instance, the microstrain-inducing manifold 512 may be inverted such that the first side 513 of the mat 558 is placed against the wound and the shaped projections 526 extend towards the sealing member (not shown). Thus, the microstrain-inducing manifold 512 may assist in perfusion and fluid removal (via the apertures 560) without also increasing microstrain within the wound via the shaped projections 526.

Figure 7:
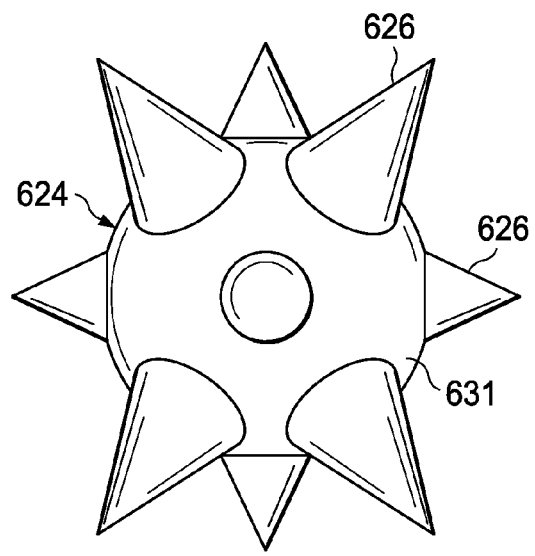
FIG. 7 is a schematic, side view of an illustrative, non-limiting embodiment of a microstrain-inducing manifold.

Referring now primarily to FIG. 7, an illustrative, non-limiting embodiment of a microstrain-inducing manifold member 624 for use with a reduced-pressure wound treatment system, such as the reduced-pressure wound treatment system 100 in FIG. 1, is shown. A microstrain-inducing manifold may be formed by a plurality of microstrain-inducing manifolds 624. Each microstrain-inducing manifold member 624 has one or more shaped projections 626 extending from a surface 631. Unlike the reduced-pressure wound treatment system 100 of FIGS. 1-3B, the microstrain-inducing manifold members 624 are not interconnected by a network of connecting members. Rather, a plurality of microstrain-inducing manifold members 624 may be poured into a wound whereby they work together to form the microstrain-inducing manifold in the wound (in situ) and whereby the shaped projections 626 of the microstrain-inducing manifold members 624 contact the wound to create microstrain therein. The plurality of microstrain-inducing manifold members 624 may fill the entire wound. Alternatively, the plurality of microstrain-inducing manifold members 624 may partially fill the wound, and, optionally, an alternative manifold may be placed atop the microstrain-inducing manifold members 624 to fill the wound.

In another alternative, the microstrain-inducing manifold members 624 may have a coating of material that allows the microstrain-inducing manifold members 624 to fuse or sinter in situ to one another and form a single, integral manifold. Non-limiting examples of coatings include the following: any water soluble, swellable, or softenable material, including polymers such as poly vinyl alcohol and its copolymer, polyvinyl pyrrolidone and its copolymers, polyethylene oxide and its copolymers, polypropylene oxide and its copolymers, hydroxyl, carboxyl, and sulphonyl containing polymers (e.g., hydroxyl ethyl acrylate, carboxyl methyl cellulose, acrylamido methyl propane sulphonic acid and its salts), alginates, gums (e.g. xanthan and guar), other hydrogels and hydrocolloids.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in a connection to any one embodiment may also be applicable to any other embodiment.

We claim:

1. A method for treating a tissue site with reduced pressure, comprising:
   placing a manifold structure proximate the tissue site, wherein the manifold structure comprises:
   a plurality of spaced longitudinal members,
   at least one shaped projection coupled to at least one of the longitudinal members for creating a microstrain at the tissue site,
   the at least one shaped projection comprising a columnar member having a distal end, and an enlarged member positioned at the distal end of the columnar member,
   wherein the columnar member has a first outer diameter and wherein the enlarged member has a second outer diameter, and
   wherein the second outer diameter of the enlarged member is greater than the first outer diameter of the columnar member;
   disposing a sealing member over the manifold structure;
   forming a fluid seal between the sealing member and the tissue site; and
   providing reduced pressure to the manifold structure whereby the at least one shaped projection creates microstrain at the tissue site;
   wherein the manifold structure deforms more in a first direction than in a second direction upon being subjected to a reduced pressure, and wherein the first direction and second direction are substantially coplanar.

2. The method of claim 1, wherein the longitudinal members are substantially parallel with one another.

3. The method of claim 1, wherein at least one longitudinal member includes two or more shaped projections for creating a microstrain at the tissue site.

4. The method of claim 1, wherein the longitudinal members are interconnected by a plurality of lateral interconnecting members.

5. The method of claim 1, further comprising a plurality of lateral interconnecting members and wherein the lateral interconnecting members are coupled to the plurality of longitudinal members.

6. The method of claim 1, wherein the manifold structure is deformable.

7. The method of claim 1, wherein the enlarged member has a spherical shape.

8. The method of claim 1, wherein the plurality of longitudinal members of the manifold structure are adapted to move laterally towards one another to deform the manifold structure in the first direction, the first direction being substantially perpendicular to the longitudinal members.

* * * * *